(12) United States Patent
Liang

(10) Patent No.: US 8,288,691 B2
(45) Date of Patent: Oct. 16, 2012

(54) WARMER DEVICE AND OPERATING METHOD THEREOF

(76) Inventor: ShengQuan Liang, Foshan (CN)

(*) Notice: Subject to any disclaimer, the term of this patent is extended or adjusted under 35 U.S.C. 154(b) by 1330 days.

(21) Appl. No.: 11/895,439

(22) Filed: Aug. 23, 2007

(65) Prior Publication Data

US 2008/0245785 A1     Oct. 9, 2008

(30) Foreign Application Priority Data

Apr. 6, 2007   (CN) ............... 2007 1 0074814

(51) Int. Cl.
*H05B 3/34* (2006.01)
*F24H 7/00* (2006.01)
(52) U.S. Cl. ...................... 219/528; 392/339
(58) Field of Classification Search .......... 219/528, 219/529, 530, 538–549; 392/339–341
See application file for complete search history.

(56) References Cited

U.S. PATENT DOCUMENTS 5,730,721 A * 3/1998 Hyatt et al. ............... 604/500
6,031,212 A * 2/2000 Westerman et al. ........ 219/535

* cited by examiner

*Primary Examiner* — Sang Paik
(74) *Attorney, Agent, or Firm* — Raymond Y. Chan; David and Raymond Patent Firm

(57) ABSTRACT

A warmer device includes a protection device, a rechargeable warmer bag and a monitoring device. The rechargeable warmer bag includes a bag, a heating unit, a charging unit, and a monitoring unit for protecting the rechargeable warmer bag. When the rechargeable warmer bag is being charged in the cavity of the protection device, the rechargeable warmer bag is monitored by the monitoring device. When the rechargeable warmer bag is heated to be over expanded, the monitoring device disconnects the external circuit to protect the rechargeable warmer bag from being broken or explosion. When the rechargeable warmer bag is being used, the rechargeable warmer bag and the monitoring device are separated.

1 Claim, 19 Drawing Sheets

A-A

WARMER DEVICE AND OPERATING METHOD THEREOF

BACKGROUND OF THE PRESENT INVENTION

1. Field of Invention

The present invention relates to a warmer device, and more particularly to a warmer device and operating method thereof, wherein the warmer device comprises a protection device, a rechargeable warmer bag, and a monitoring device, wherein the rechargeable warmer bag comprises a bag, a heating unit, a charging unit and the monitoring device is arranged in the protection device with respect to the rechargeable warmer bag so that the rechargeable warmer bag is monitored and control by the monitoring device while the rechargeable warmer bag is being charged in the cavity of the protection device. Therefore, when the rechargeable warmer bag is heated to be over expanded, the monitoring device cuts the power supply of charging unit of the rechargeable warmer bag. However, when the rechargeable warmer bag is being used, the rechargeable warmer bag and the monitoring device are separated.

2. Description of Related Arts

As everyone knows, it is very cold in winter, so people have invented various kinds of warmer device to keep warm in cold days. Some kinds of warmer device are huge, and inconvenient to carry out.

There is a kind of small and portable warmer device, called warm water bag comprising a bag and a sealing cover, wherein the bag is made of water proof material such as plastic. The bag has an inner cavity and an opening, and the sealing cover is to cover the opening. In order to use it, the user has to heat a certain mount of liquid, such as water in a stove or other devices, and fill the warm liquid into the inner cavity of the bag. At last, cover the sealing cover onto the opening to seal the cavity so as to keep the liquid inside.

The warm water inside the cavity conducts or radiate the heat to the outside constantly, so that the user can put the warm water bag to part of body where is cold, such as hands or feet to keep warm.

However, an essential disadvantage of the traditional warm water bag is inconvenient to use. Since the liquid radiate its heat, the temperature is decreasing at the same time. The warm water bag can no longer provide heat when the temperature drops down to a level similar to the body temperature. The user has to pour out the liquid in the cavity and refill warm water repeatedly. It is very inefficient and inconvenient.

Some inventors create a kind of rechargeable warmer bag, comprising a bag, a power supply unit, and a warmer device, wherein the bag has a cavity with a predetermined amount of liquid therein and the warmer device which is positioned in the cavity of the bag comprises a heating tube and a socket connecting to the power supply unit.

In order to use the rechargeable warmer bag, connect it to the power supply, so that the electricity is converted to heat in the heating tube and the heating tube conducts heat to the liquid in the cavity. After a certain time, the liquid is warm enough, the user cuts off the power supply to use the rechargeable warmer bag.

But, as mentioned above, the liquid in the cavity will expand when the rechargeable warmer bag is being charged. The higher the temperature, the more it expands. When it expands too much, the pressure in the bag is rising. As the pressure is rising to a certain extent, the bag will be broken and the hot liquid inside will be leaked or even sprayed out. If this is happened, the conventional rechargeable warmer bag contains safety problems and causes dangerous to the user's life. This is a main disadvantage of the rechargeable warmer bag.

SUMMARY OF THE PRESENT INVENTION

A main object of the present invention is to provide a warmer device and operating method thereof, wherein the special design is a breakthrough of traditional warmer device.

Another object of the present invention is to provide a warmer device and operating method thereof, which is designed to be convenient and portable.

Another object of the present invention is to provide a warmer device and operating method thereof, which is designed to assure its operation safety.

Accordingly, in order to accomplish the above object, the present invention provides a warmer device, comprising:

a protection device having a protection cavity therein; and a rechargeable warmer bag arranged to be charged in the protection device in such a manner that the rechargeable warmer bag is disposed in the protection cavity of the protection device during charging and the rechargeable warmer bag is removed from the protection device for use.

The rechargeable warmer bag comprises:

a bag, having an outer surface and an inner surface defining a sealed cavity receiving a predetermined amount of liquid therein;

a heating unit which is disposed in the liquid in the sealed cavity of the bag comprising a plurality of heaters;

a charging unit, which is connected with the heating unit and disposed between the bag and the heating unit, comprising a charging connector and a connecting wire; and a monitoring device arranged in the protection device with respect to the rechargeable warmer bag so as to monitor the rechargeable warmer bag and cut off the power supply of the charging unit of the rechargeable warmer bag when the rechargeable warmer bag is over-expanded, and that when the rechargeable warmer bag is in use, the rechargeable warmer bag and the monitoring device are separated.

Therefore, the rechargeable warmer bag must be placed in the cavity of the protection device during charging. At this moment, the rechargeable warmer bag is monitored and control by the monitoring device. If the rechargeable warmer bag is heated to be expanded to a certain extent, the rechargeable warmer bag will be in contact with the actuator and the actuator disconnects the external circuit to protect said rechargeable warmer bag from being broken or exploded. When the rechargeable warmer bag is being used, the rechargeable warmer bag is disconnected with the monitoring device.

These and other objectives, features, and advantages of the present invention will become apparent from the following detailed description, the accompanying drawings, and the appended claims.

DETAILED DESCRIPTION OF THE PREFERRED EMBODIMENT

Figure 1:
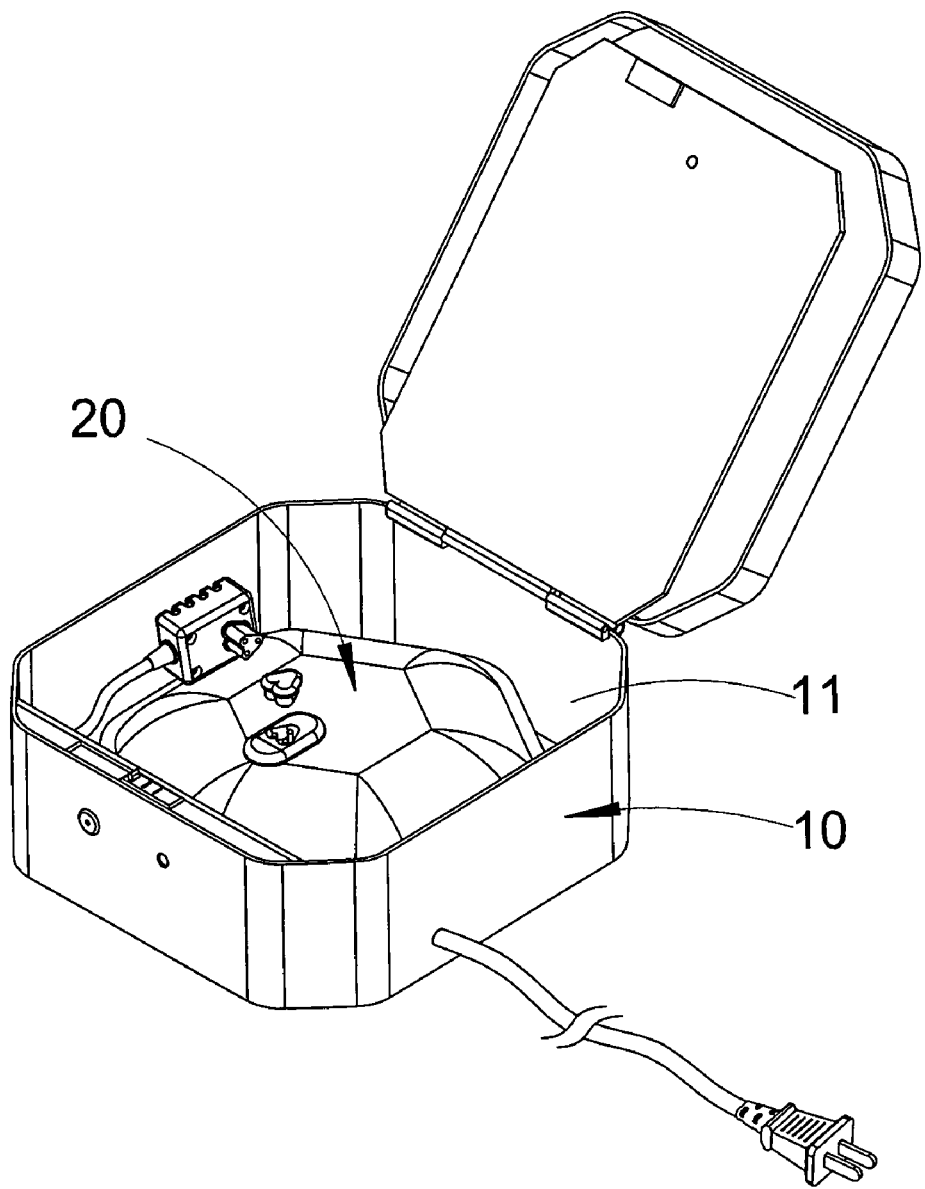
FIG. 1 is a perspective view of a charge warmer device according to a preferred embodiment of the present invention.
Figure 2:
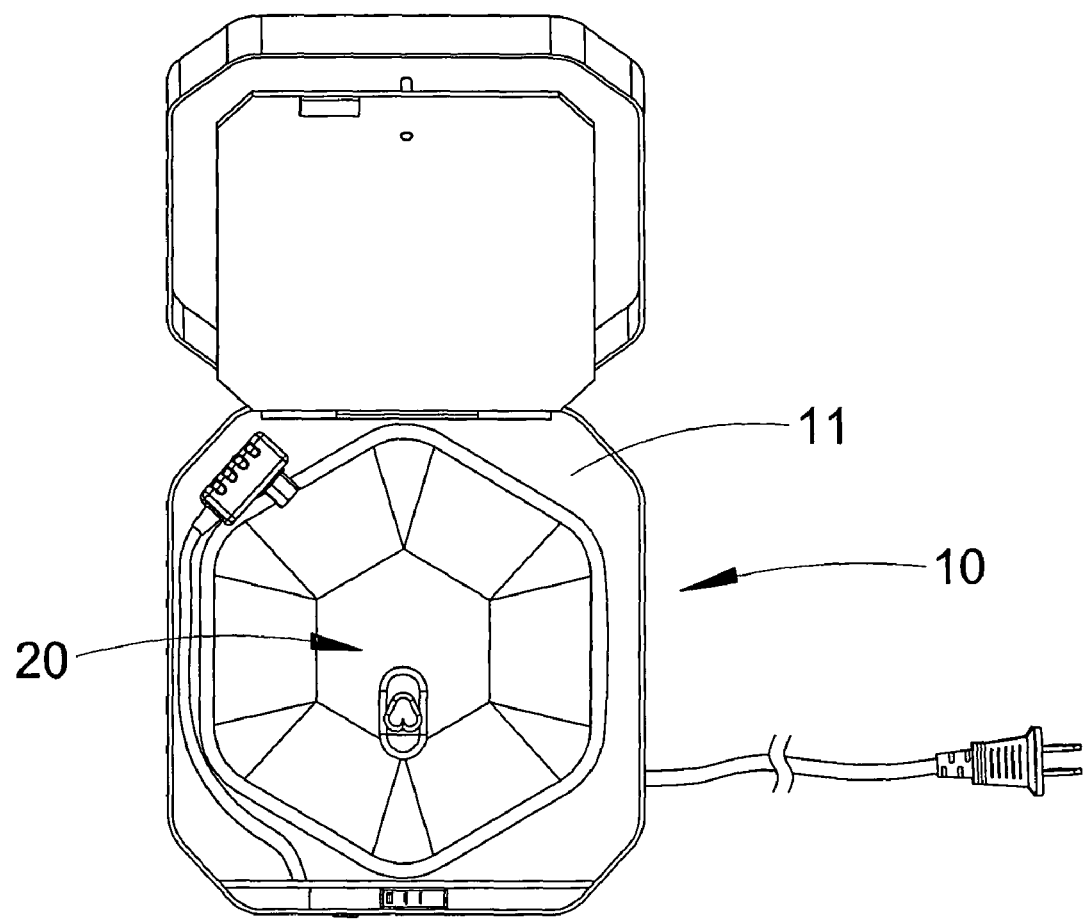
FIG. 2 is a top exterior view of the charge warmer device according to the above preferred embodiment of the present invention.
Figure 3:
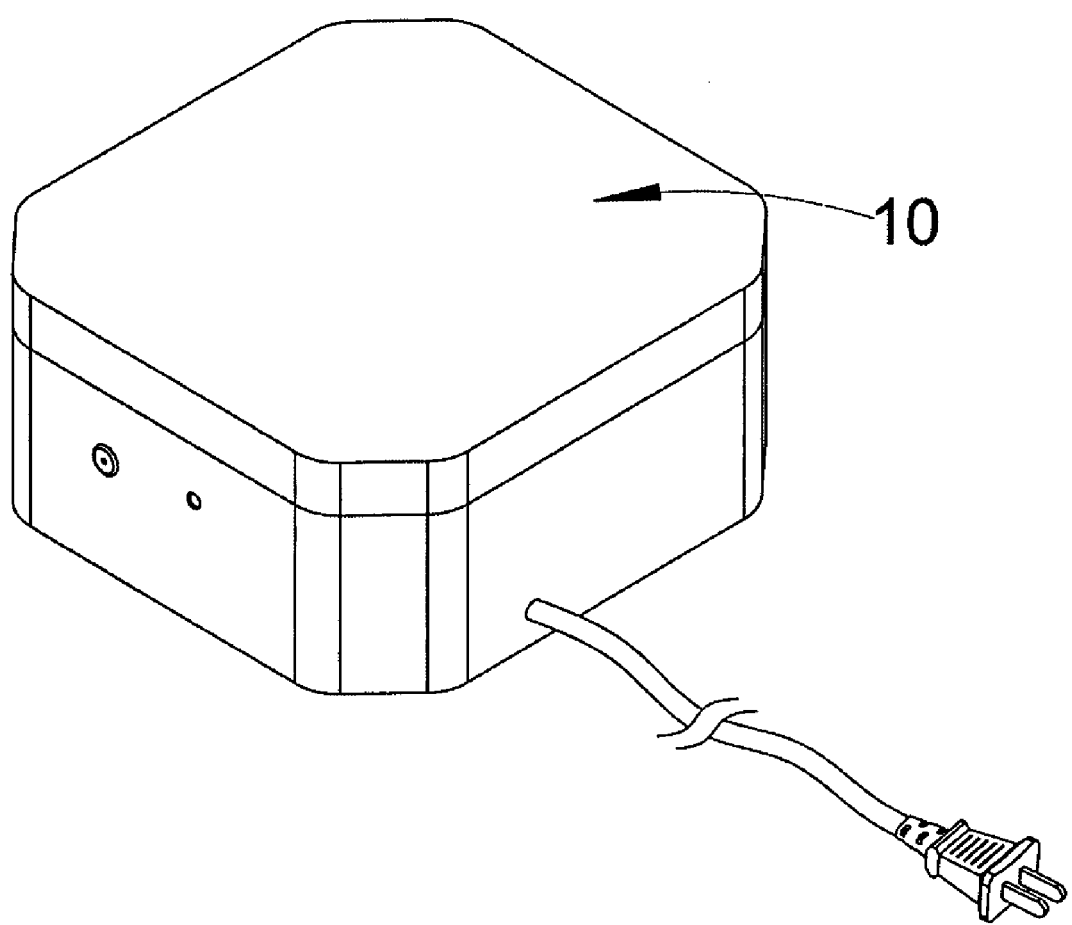
FIG. 3 is a perspective view of the charge warmer device at a closed position according to the above preferred embodiment of the present invention.
Figure 4:
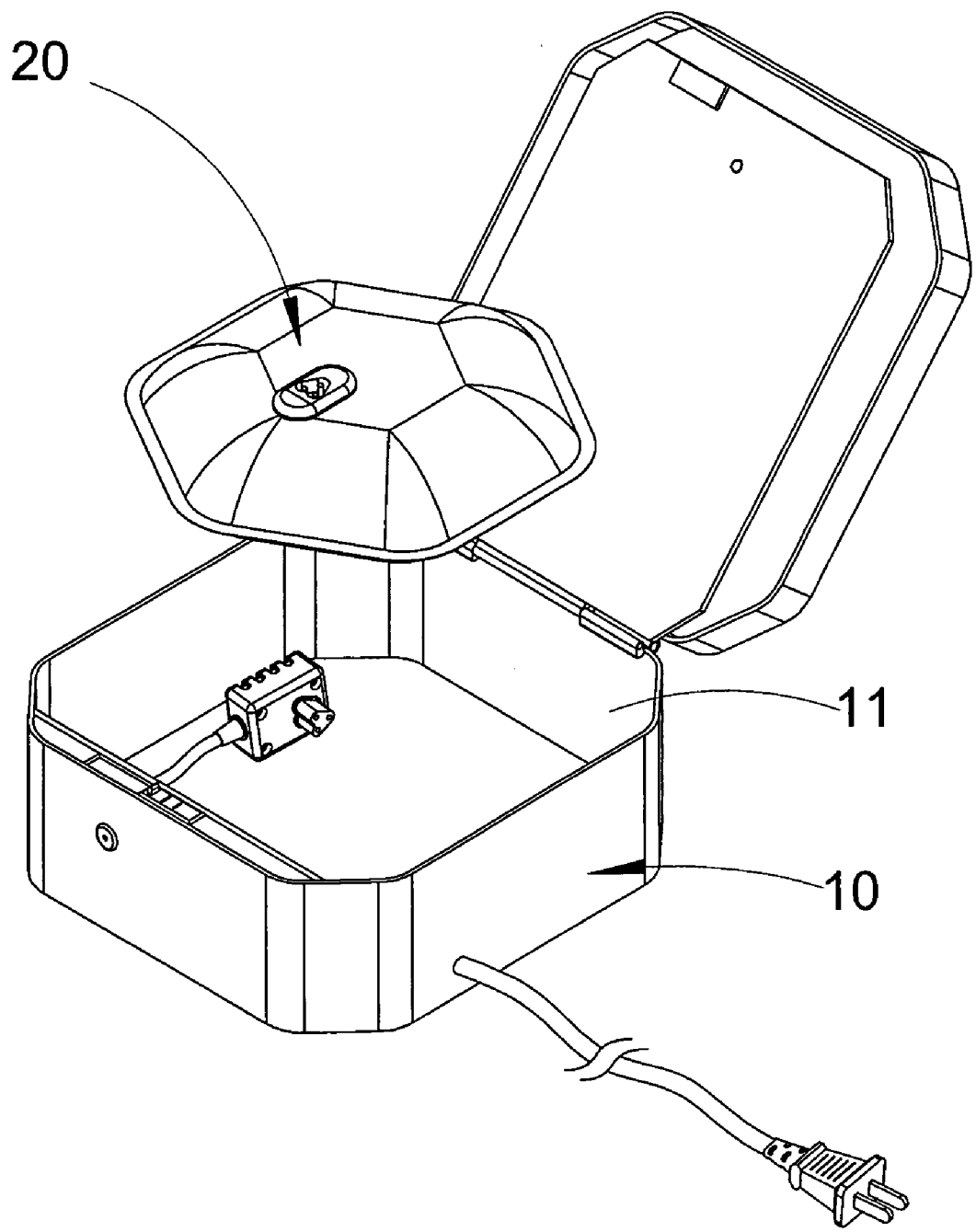
FIG. 4 is an exploded view of the charge warmer device according to the above preferred embodiment of the present invention.
Figure 5:
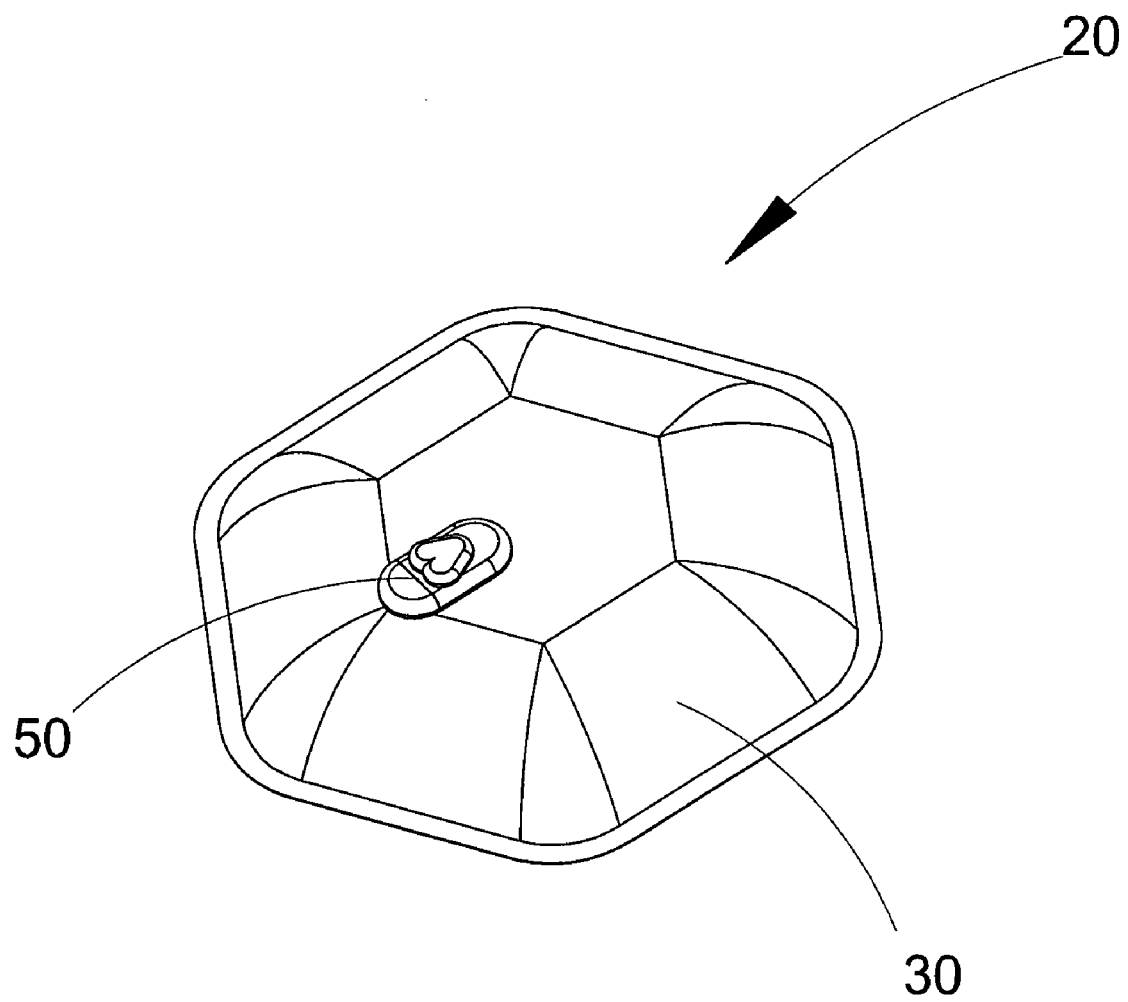
FIG. 5 is a perspective view of a rechargeable warmer bag according to the above preferred embodiment of the present invention.
Figure 6:
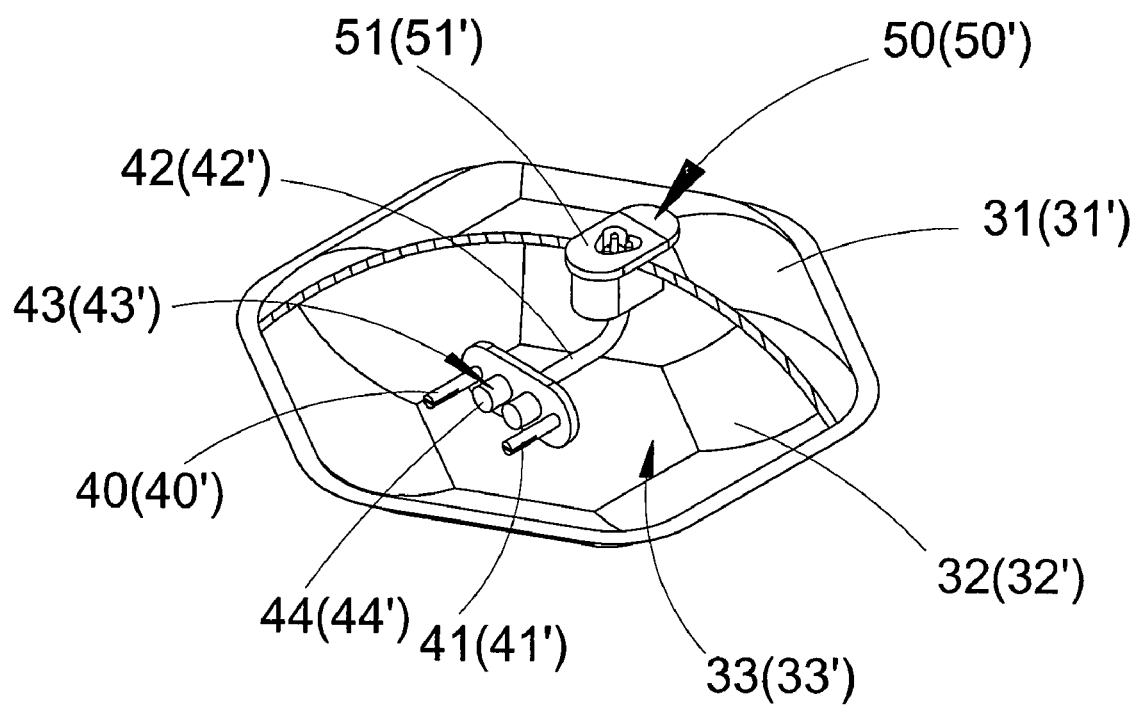
FIG. 6 is a schematic view of the rechargeable warmer bag according to the above preferred embodiment of the present invention.
Figure 7:
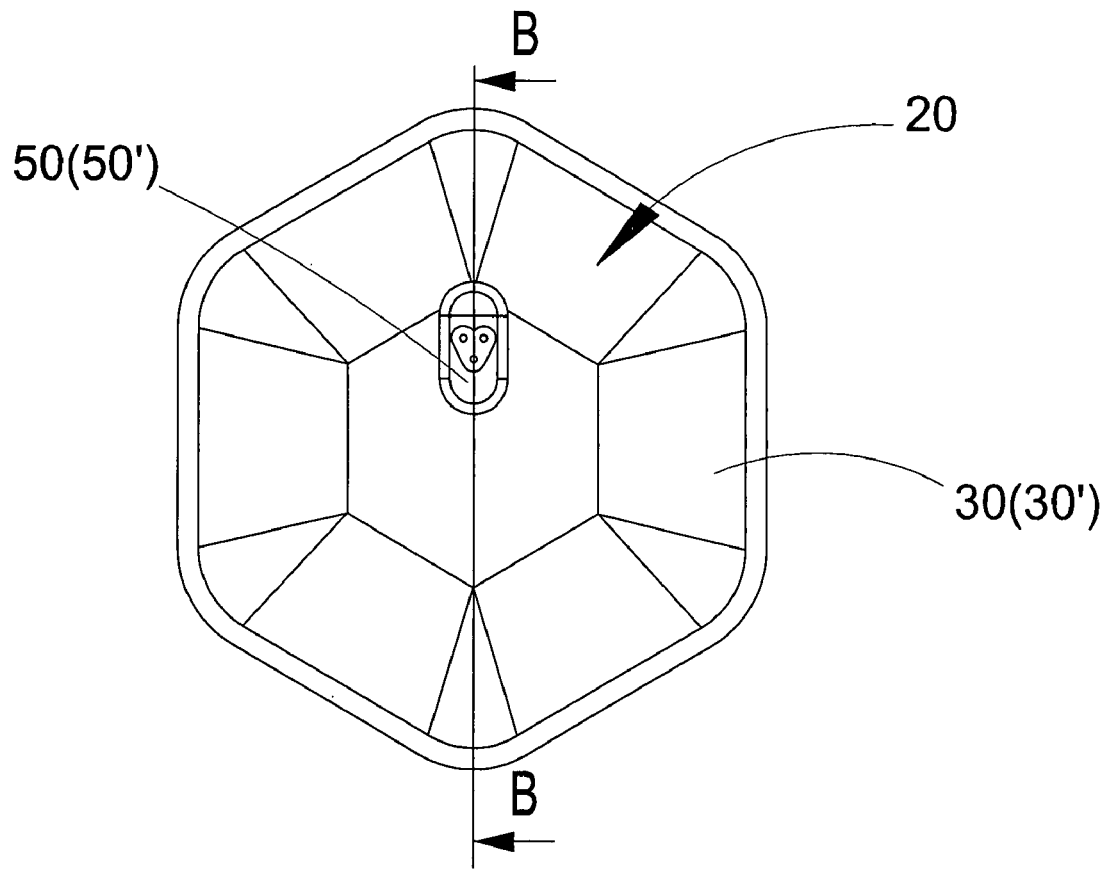
FIG. 7 is a top exterior view of the rechargeable warmer bag according to the above preferred embodiment of the present invention.

Referring to FIG. 1 to FIG. 4 of the drawings, a warmer device according to a preferred embodiment of the present invention is illustrated. The warmer device comprises a protection device 10 having an interior protection cavity 11 isolated from outside environment and a rechargeable warmer bag 20 arranged to be charged in the protection device 10.

The rechargeable warmer bag 20 is disposed in the cavity 11 of the protection device 10 during charging and removed out of the protection device 10 during operation thereof.

As shown in FIG. 5 to FIG. 8, the rechargeable warmer bag 20 further comprises:

a bag 30 having an outer surface 31 and an inner surface 32 defining a sealed cavity 33 receiving a predetermined amount of liquid 34 therein;

a heating unit 40 which is disposed in the liquid 34 in the sealed cavity 33 of the bag 30 comprising a plurality of heaters 41;

a charging unit 50, which is connected with the heating unit 40 and positioned between the bag 30 and the heating unit 40, comprising a charging connector 51 and a connecting wire; and a monitoring device 60 arranged in the protection device 10 with respect to the rechargeable warmer bag 20 so as to monitor the rechargeable warmer bag 20 and cut off the power supply of the charging unit 50 of the rechargeable warmer bag 20 when the rechargeable warmer bag 20 is over-expanded, and that when the rechargeable warmer bag 20 is in use, the rechargeable warmer bag 20 and the monitoring device 60 are separated.

As shown in FIG. 9 to FIG. 12, the protection device 10 comprises a box 12 and a box cover 13 for covering the box 12, wherein the box 12 has an outer surface 122 and an inner surface 121 defining a cavity 123 separated from the outer space by the box cover 13.

The protection device 10 further comprises a pivot 14 for pivotally connecting the box 12 and the box cover 13.

The protection device 10 further comprises a buckle 15 between the box 12 and the box cover 13 for securing the box cover 13 on the box 12 so as to separate the cavity 123 of the box 12 from the outer space.

The rechargeable warmer bag 20 should be placed in the cavity 123 of the protection device 10 when being charged.

Figure 13:
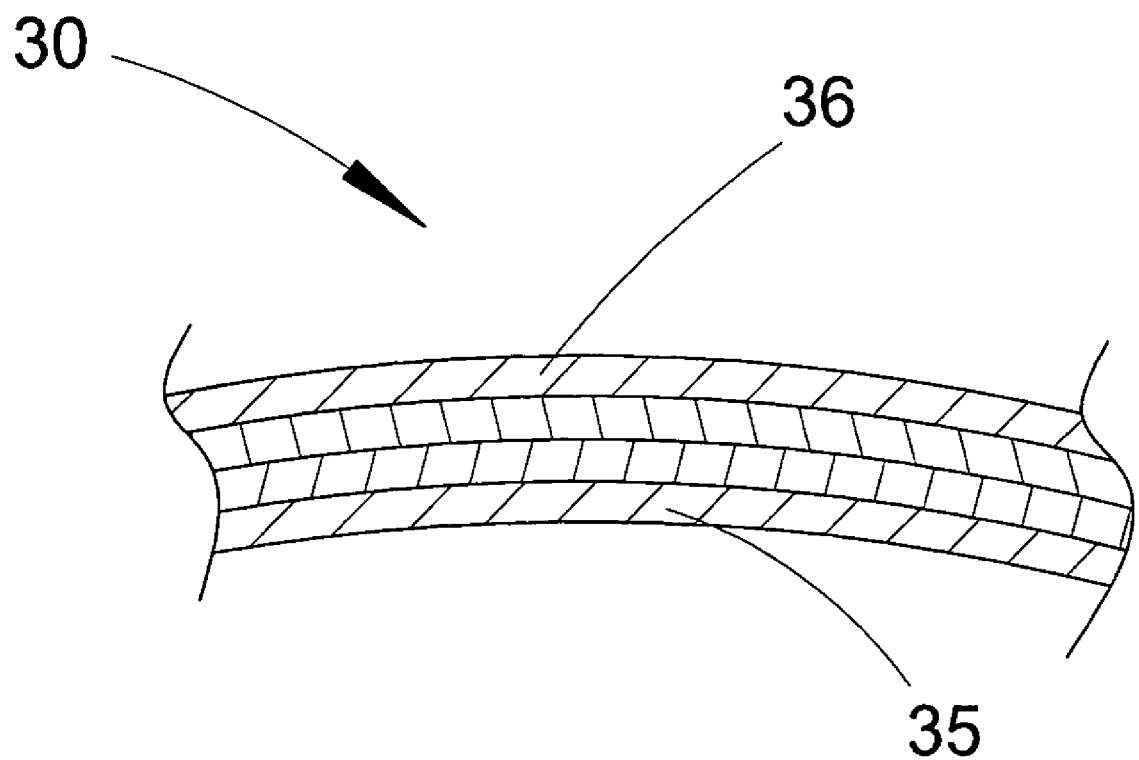
FIG. 13 is a schematic view of the bag according to the above preferred embodiment of the present invention.

The bag is made of a water-proof material. Further more, the bag is made of a soft water-proof material. As shown in FIG. 13, the bag 30 comprises a plurality of layers, wherein the innermost layer 35 is made of water-proof material that can seal the liquid 34 within the sealed cavity 33 of the bag 30, and the outermost layer 36 is made of soft material so as to be touched by the user skin.

Figure 8:
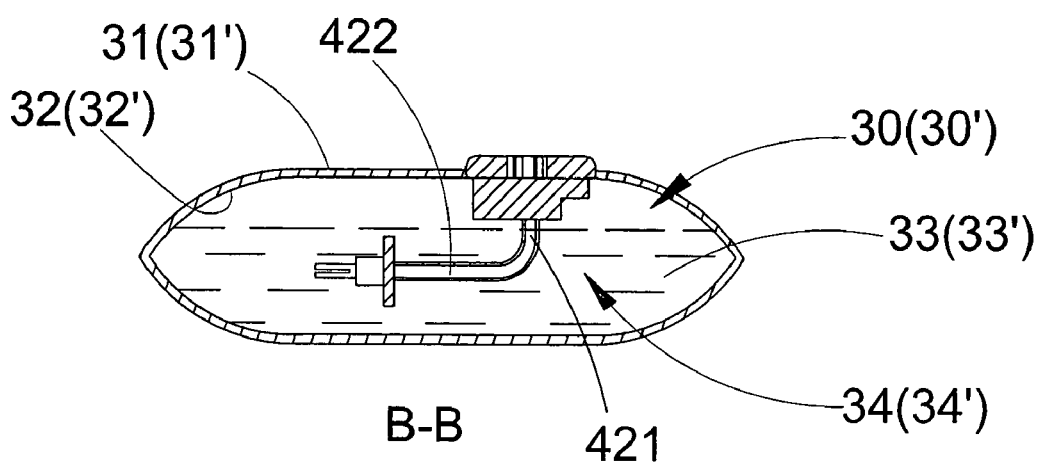
FIG. 8 is a B-B sectional view of the rechargeable warmer bag according to the above preferred embodiment of the present invention.

As shown in FIG. 8, the heating unit 40 in the bag 30 further comprises a connecting tube 42 and the temperature control device 43.

The temperature control device 43, which is connected between the heaters of the heating unit 40, comprises a plurality of temperature controllers 44 with different rated temperature for cutting off the power supply. The temperature control device 43 monitors the temperature of the liquid 34 in the bag 30 in real-time during the rechargeable warmer bag 20 is being charged. When the temperature is up to the rated temperature of any temperature controller 44, the temperature control device cuts off the power supply of the charging unit 50.

The following is one of the temperature safety protection arrangements according to the present invention.

The connecting tube 42 is securely connected between the heaters 41 and the charging connector 51 of the charging unit 50 so as to support the heaters 41 to be positioned within the sealed cavity 33 of the bag 30. When the rechargeable warmer bag 20 is being charged, the connecting tube 42 supports the heaters to ensure that the heaters are disposed in the sealed cavity 33 of the bag 30 and surrounded by the liquid 34 in the cavity 33.

As the heater 41 of the heating unit 40 converts the electricity to the heat, and conducts the heat to the liquid 34 in the bag 30, the temperature of the liquid 34 raises and the volume of the liquid 34 is expanded. At this moment, the gas generated inside the bag 30 is expanded too. According to the proportional relation of the gas expansion and liquid expansion when heated, the gas expansion velocity is faster than liquid expansion velocity, so that the gas in the cavity squeezes liquid 34 in the cavity. Gradually, the heater 41 of the heating unit 40 separates from the liquid 34, as the liquid level falls due to the rising of the liquid temperature, and then the charge warmer device 20 is cut off from the power supply.

The following is another temperature safety protection arrangement according to the present invention.

Furthermore, the connecting tube 42 comprises a vertical tube 421 and a transverse pole 422.

The charging connector 51 of the charging unit 50 can be embodied as a socket.

Figure 14:
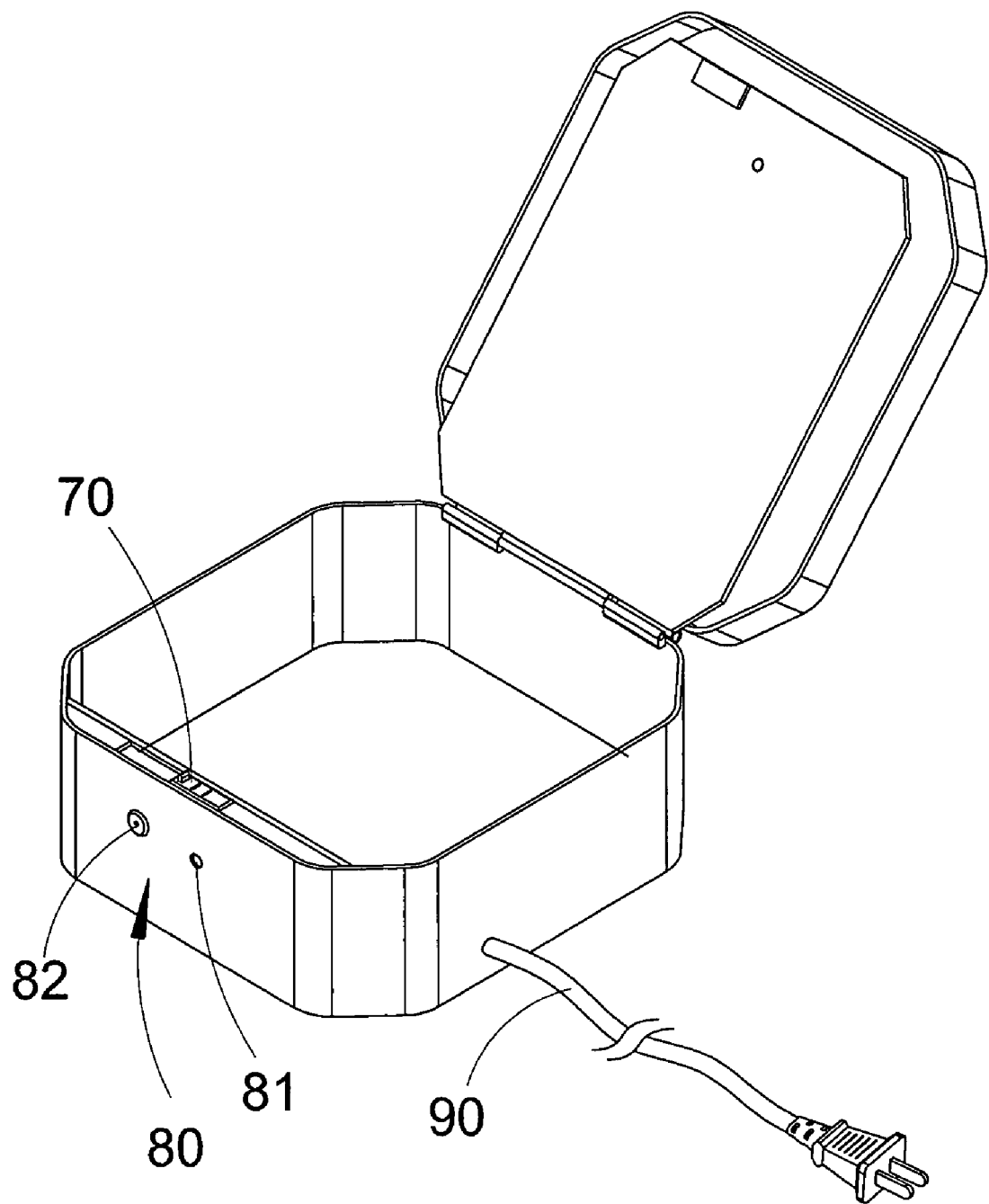
FIG. 14 is a schematic view of a monitoring device of the protection device according to the above preferred embodiment of the present invention.
Figure 15:
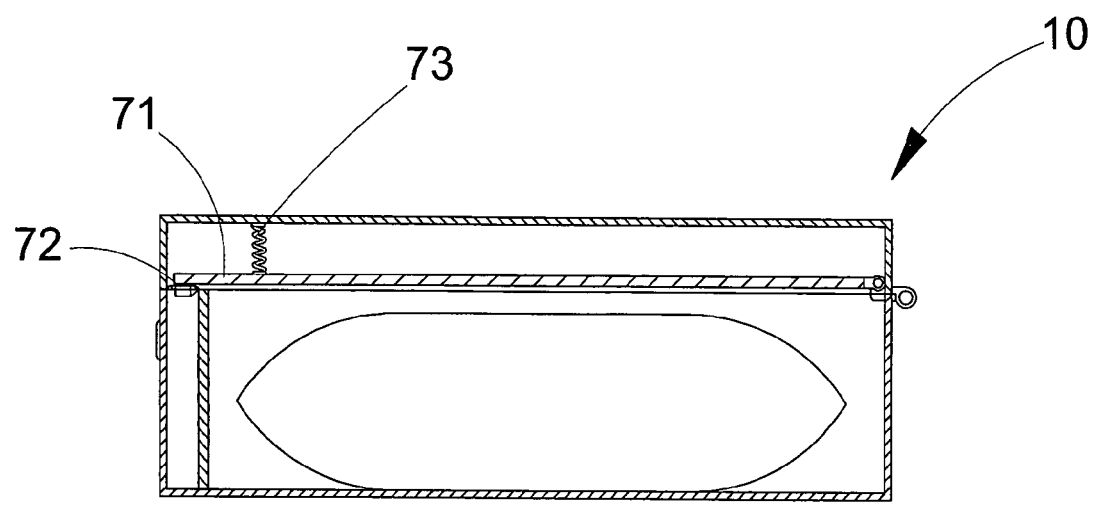
FIG. 15 is a schematic view of a protection device with a rechargeable warmer bag therein according to the above preferred embodiment of the present invention.
Figure 16:
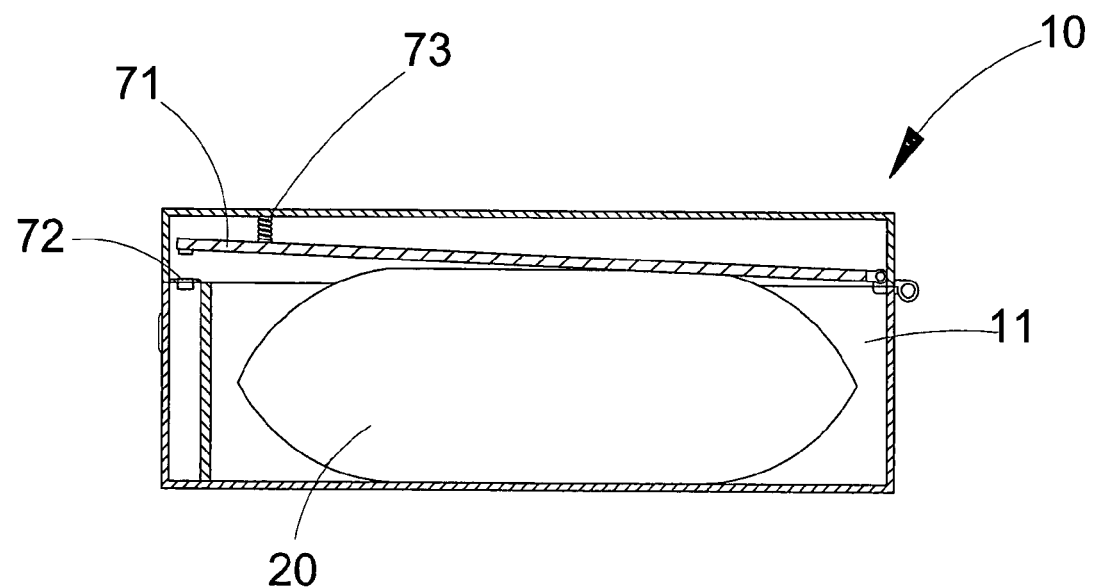
FIG. 16 is a schematic view of a protection device with an expanded rechargeable warmer bag according to the above preferred embodiment of the present invention.
Figure 17:
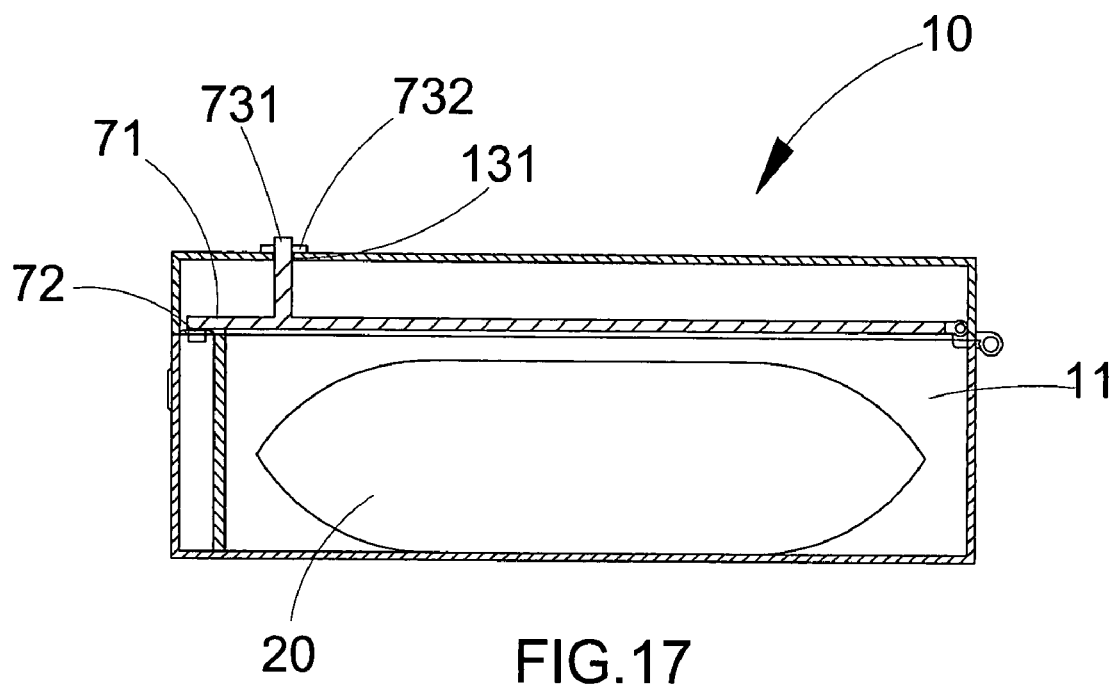
FIG. 17 is a schematic view of a protection device with a rechargeable warmer bag therein according to the above preferred embodiment of the present invention.
Figure 18:
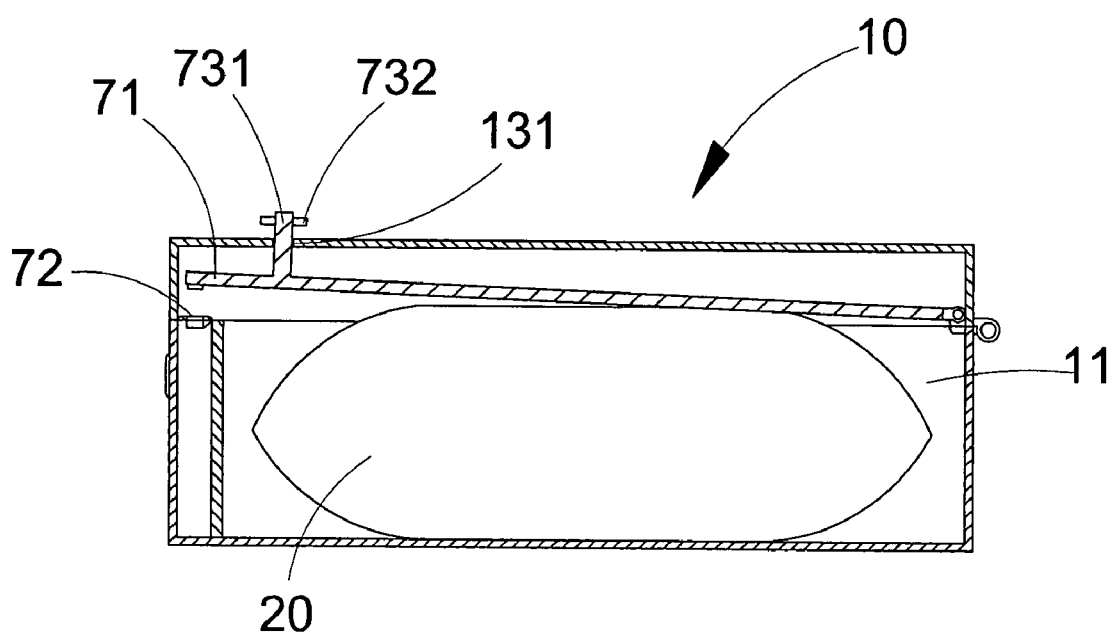
FIG. 18 is a schematic view of a protection device with an expanded rechargeable warmer bag according to the above preferred embodiment of the present invention.

As shown in FIG. 14, the monitoring device 60 disposed in the cavity 11 of the protection device 10 comprises an actuator 70, an altering device 80, and an external circuit 90.

As shown in FIG. 15 to FIG. 18, the actuator 70 is connected to the external circuit 90 and disposed in the cavity 11. When the rechargeable warmer bag 20 is being charged in the cavity 11 of the protection device 10, the rechargeable warmer bag 20 is monitored and controlled by the monitoring device 60. If the rechargeable warmer bag 20 is heated to be over-expanded, the rechargeable warmer bag 20 will be in contact with actuator 70 and then the actuator 70 disconnects the external circuit 90 so as to protect the rechargeable warmer bag 20 from being broken or explosion.

The actuator 70 comprises an actuator board 71, an actuator switch 72 and a connecting element 73, wherein the actuator board 71 is disposed in the cavity 11 of the protection device 10 and placed above the rechargeable warmer bag 20 when being charged in the cavity 11 of the protection device.

Furthermore, the actuator board 71 is placed in the box cover 13 of the protection device 10.

One end of the actuator board 71 is pivotally connected to the top of the protection device 10.

In addition, the actuator switch 72 and the connecting element 73 are provided on the other end of the actuator board 71 and the actuator switch 72 is connected to the external circuit 90.

The connecting element 73 can be embodied as an elastic element, such as a spring, which is connected to the box cover 13 of the protection device 10. When the rechargeable warmer bag 20 is over expanded during charging in the protection device 10, the bag 30 is expanded upward to touch the actuator board 71 and the connecting element 73 on the other end of the actuator board 71 is compressed. And then the actuator switch 72 disconnects with the external circuit 90 to cuts off power supply so as to stop charging the rechargeable warmer bag 20 to avoid the over expansion of the bag 30.

Alternatively, the connecting element 73 can be embodied a hard connecting pole, comprising a fixed pole 731 and a retaining sheet 732. The box cover 13 of the protection device 10 has a through hole 131 therein for receiving the fixed pole 731. The retaining sheet 732 is positioned on the top of the fixed pole 731, bigger than the through hole 131 in size.

As mentioned above, the connecting element 73 comprises a plurality of elastic elements, each having one end connected to the top of the protection device 10 and another end connected to the actuator board 71. When the rechargeable warmer bag 20 is being charged in the cavity 11 of the protection device 10, the actuator board 71 is positioned on the upper side of the protection device relative to the rechargeable warmer bag 20.

The actuator switch 72 is positioned on the actuator board 71, and connects to the external circuit 90.

Further more, the elastic element is embodied as a spring.

Figure 19:
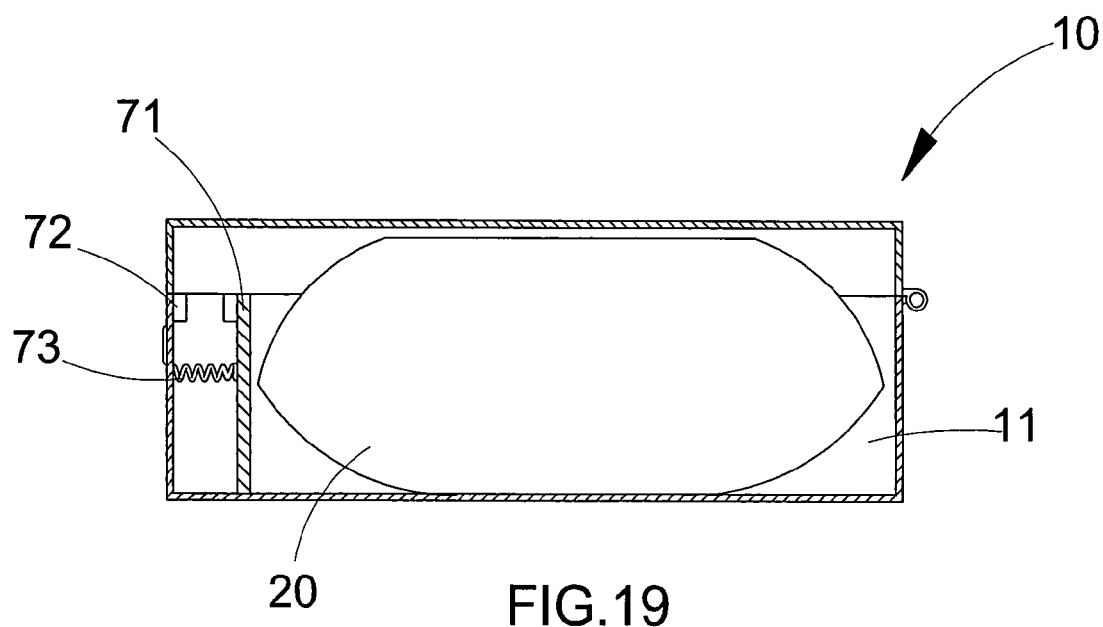
FIG. 19 is a schematic view of a protection device with a rechargeable warmer bag therein according to the above preferred embodiment of the present invention.
Figure 20:
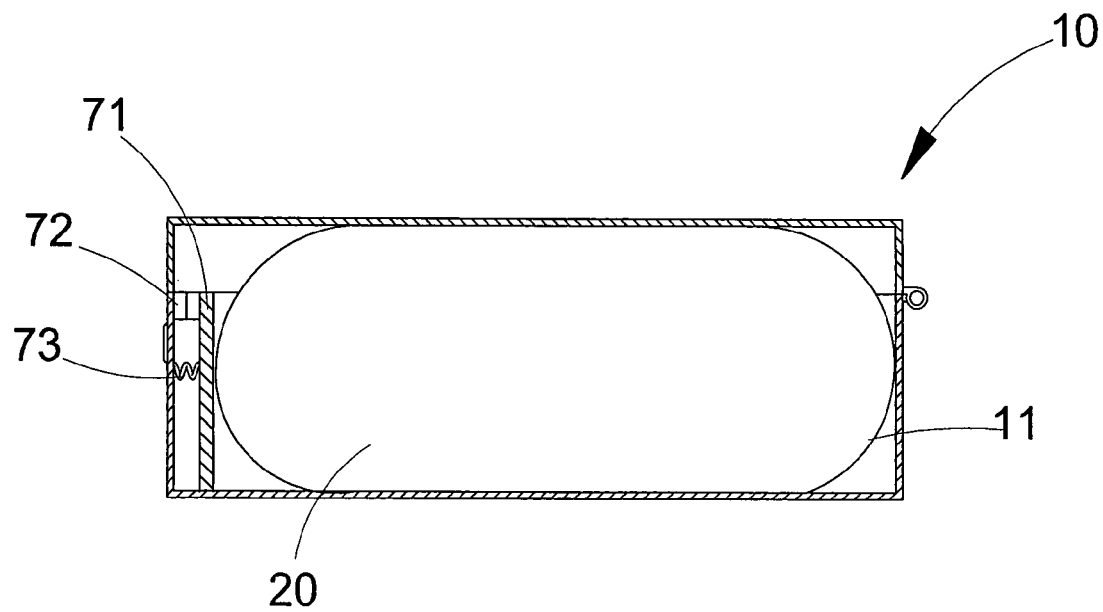
FIG. 20 is a schematic view of a protection device with an expanded rechargeable warmer bag according to the above preferred embodiment of the present invention.

As shown in FIG. 19 to FIG. 20, the actuator 70 comprises an actuator board 71 disposed in the cavity 11 of the protection device 10, an actuator switch 72, and a connecting element 73. When the rechargeable warmer bag 20 is being charged in the cavity 11 of the protection device 10, the actuator 71 is positioned surrounding the rechargeable warmer bag 20 and the actuator switch 72 is positioned between the actuator board 71 and the external circuit 90.

The connecting element 73 is connected with the side wall of the protection device. If rechargeable warmer bag 20 is heated to be over expanded during charging in the protection device 10, the bag 30 expands to touch the actuator board 71 and compress the connecting element 73, and then the actuator switch 72 disconnects the external circuit 90 to avoid the bag 30 to be over expanded.

Figure 21:
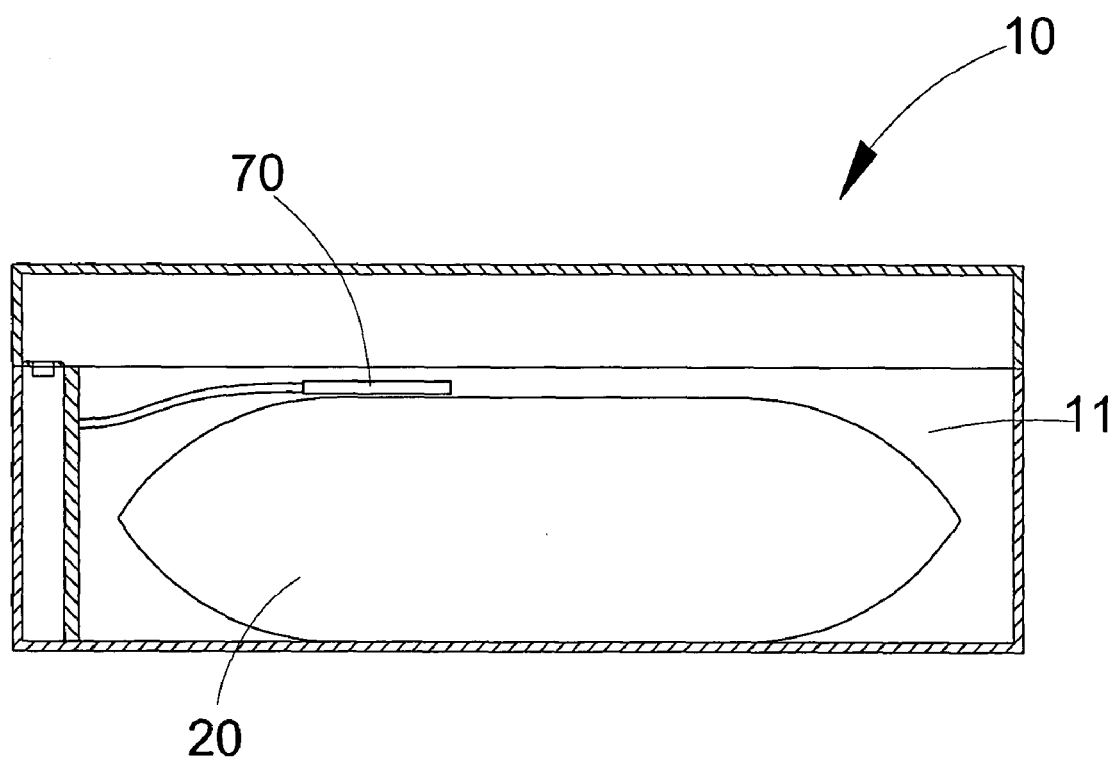
FIG. 21 is a schematic view of a protection device with a rechargeable warmer bag therein according to the above preferred embodiment of the present invention.

As shown in FIG. 21, the monitoring device 60 positioned in the cavity 11 of the protection device 10 comprises an actuator 70, an alerting device 80, and an external circuit 90, wherein the actuator 70 is connected with the external circuit 90, and is positioned in the cavity 11 of the protection device. The actuator 70 can be embodied as a temperature measuring meter. When the rechargeable warmer bag 20 is being charged in the cavity 11 of the protection device, the rechargeable warmer bag 20 is monitored by the monitoring device 60. The actuator 70 has a plurality of preset value for cutting off the power. When the rechargeable warmer bag 20 is heated to be over expanded, and the temperature of the rechargeable warmer bag 20 is up to the preset value, the actuator 70 disconnects the external circuit 90 to protect the rechargeable warmer bag 20 for explosion.

The altering device 80, which is connected with the actuator 70 and the external circuit 90, comprises a visional altering device 81 and an audio alerting device 82. When the rechargeable warmer bag 20 is charged in the cavity 11 of the protection device, the rechargeable warmer bag 20 is monitored by the monitoring device 60. When the rechargeable warmer bag 20 is heated to be over expanded, the actuator 70 disconnects the external circuit 90. At the same time, the actuator 70 conducts the visional alerting device 81 and the audio alerting device 82 with the external circuit 90, so the visional alerting device 81 is illuminating and the audio alerting device 82 produces sound to alert the user.

Figure 22:
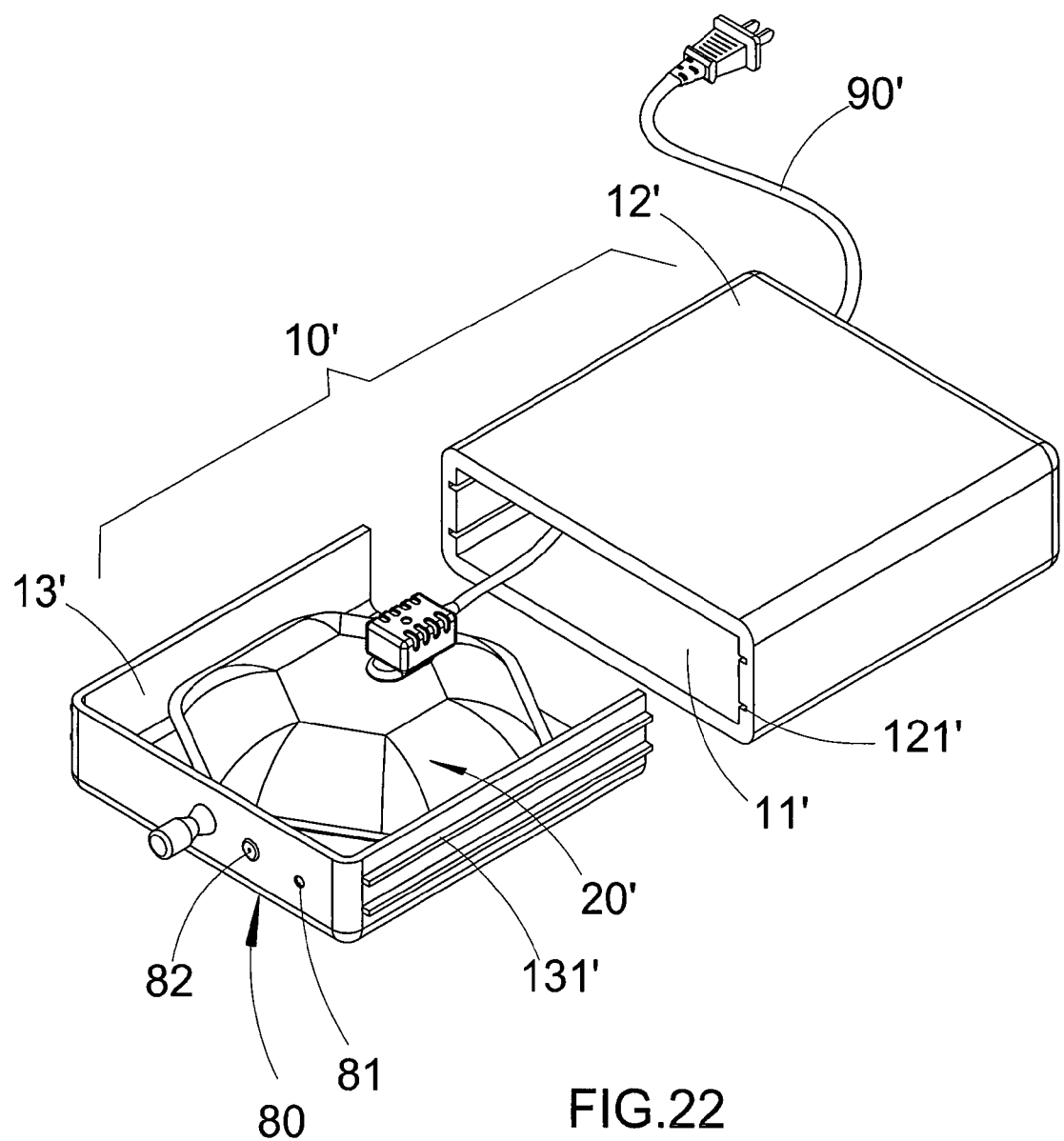
FIG. 22 is a perspective view of an alternative mode of the charge warmer device according to the above preferred embodiment of the present invention.
Figure 23:
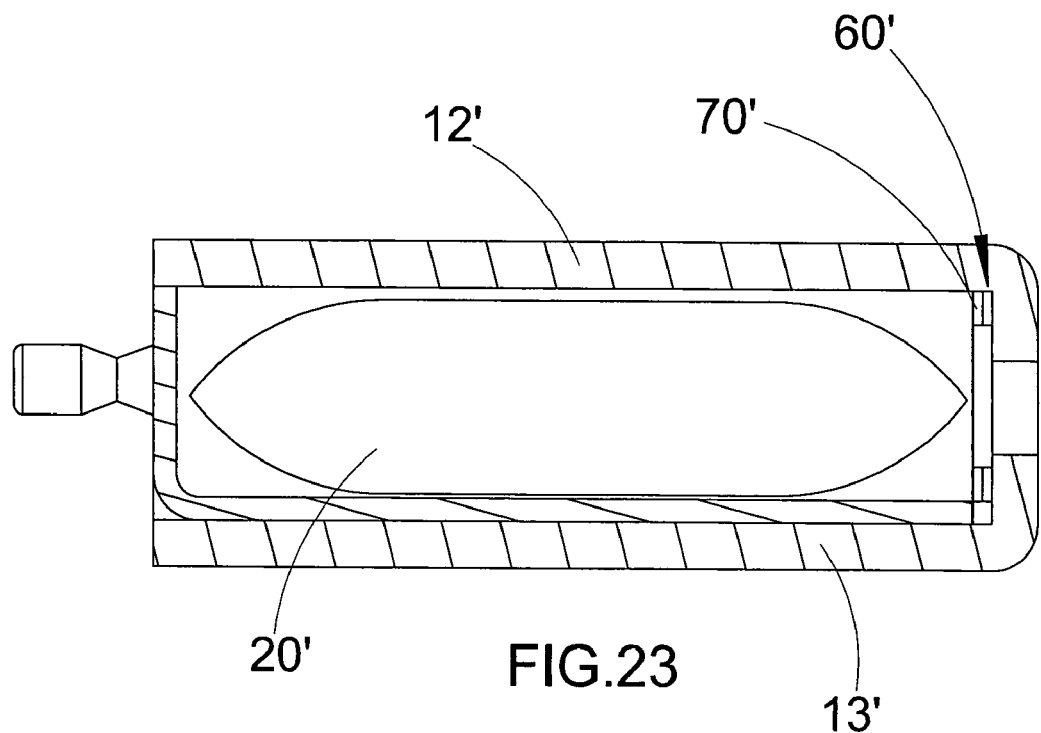
FIG. 23 is a schematic view of an alternative mode of a protection device with a rechargeable warmer bag therein according to the above preferred embodiment of the present invention.
Figure 24:
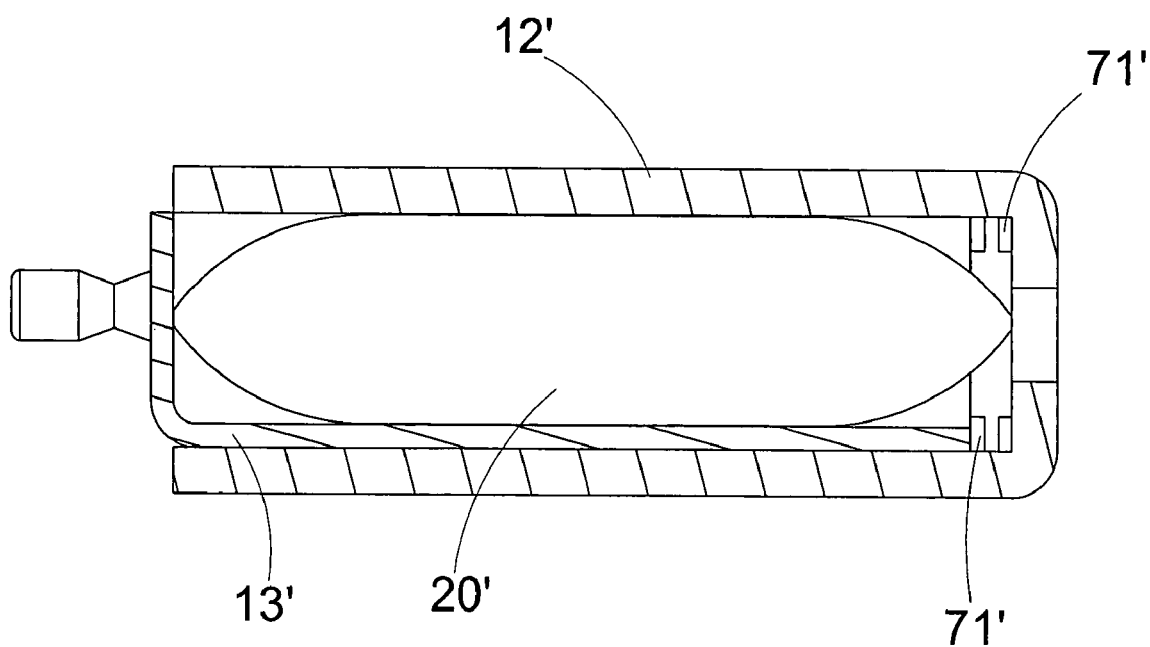
FIG. 24 is a schematic view of an alternative mode of a protection device with an expanded rechargeable warmer bag therein according to the above preferred embodiment of the present invention.

As shown in FIG. 22 to FIG. 24, another alternative mode of the present invention is illustrated.

The warmer device as shown in FIG. 22 comprises a protection device 10' having a protection cavity 11' isolated from outside environment and a rechargeable warmer bag 20' arranged to be charged in the protection device 10'.

The rechargeable warmer bag 20' is disposed in the cavity 11' of the protection device 10' during charging and removed out of the protection device 10' when the rechargeable warmer bag 20' during operation.

The rechargeable warmer bag 20' further comprises:

a bag 30', having a outer surface 31' and a inner surface 32' defining a sealed cavity 33' receiving a predetermined amount of liquid 34' therein;

a heating unit 40' which is disposed in the liquid 34' in the sealed cavity 33' of the bag 30' comprising a plurality of heaters 41';

a charging unit 50', which is connected with the heating unit 40' and disposed between the bag 30' and the heating unit 40', comprising a charging connector 51' and a connecting wire;

a monitoring device 60' arranged in the protection device 10' with respect to the rechargeable warmer bag 20' so as to monitor the rechargeable warmer bag 20' and cut off the power supply of the charging unit 50' of the rechargeable warmer bag 20' when the rechargeable warmer bag 20' is being over-expanded, when the rechargeable warmer bag 20' is in use, the rechargeable warmer bag 20' and the monitoring device 60' are separated.

The protection device 10' further comprises a container 12' and a moving unit 13' which is flexibly mounted in the container 12' and can be moved relative to the container 12'. When the rechargeable warmer bag 20' is being charged, it is positioned in the cavity 11' of the protection device 10' and in the moving unit 13'. When the rechargeable warmer bag 20' is fully charged, the moving unit 13' moves relative to the container 12', so that the rechargeable warmer bag 20' can be taken out of the protection device 10'.

As mentioned above, the container 12' comprises a plurality of slides 121', and the moving unit 13' comprises a plurality of slide rails 131' sliding to-and-fro on the slides 121' of the container 12'.

The monitoring device 60' which is disposed positioned in the cavity 11' of the protection device 10', is positioned between the container 12' and the moving unit 13'. It comprises an actuator 70', an alerting device 80', and an external circuit 90'.

The actuator 70' is connected with the external circuit 90' and positioned between container 12' and the moving unit 13'.

When the rechargeable warmer bag 20' is being charged in the cavity 11 of the protection device 10, the rechargeable warmer bag 20 is monitored by the monitoring device 60. When the rechargeable warmer bag 20' is charged to be heated, the heating bag 20' expands to compress the container to move the moving unit 12' relative to the container 12', and then the actuator 70' between the container 12' and the moving unit 13' switches off the external circuit to cut off the power supply to protect the rechargeable warmer bag 20' from being broken or explosion.

Furthermore, the actuator 70' comprises a first contact unit 71' positioned in the container 12' and a second contact unit 72' positioned on the moving unit 13'.

The altering device 80', which is connected with the actuator 70' and the external circuit 90', comprises a visional altering device 81' and an audio alerting device 82'. When the rechargeable warmer bag 20' is being charged in the cavity 11' of the protection device, the rechargeable warmer bag 20' is monitored by the monitoring device 60'. When the rechargeable warmer bag 20' is heated to be over expanded, the actuator 70' disconnects the external circuit 90'. At the same time, the actuator 70' conducts the visional alerting device 81' and the audio alerting device 82' with the external circuit 90', so that the visional alerting device 81' is illuminating and the audio alerting device 82' produces sound to alert the user.

Figure 25:
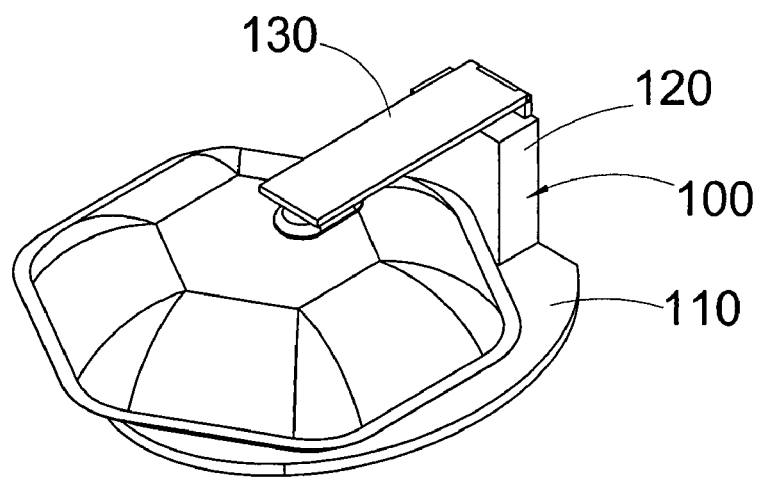
FIG. 25 is a schematic view of a first alternative mode of a protection device with a rechargeable warmer bag therein according to the above preferred embodiment of the present invention.
Figure 26:
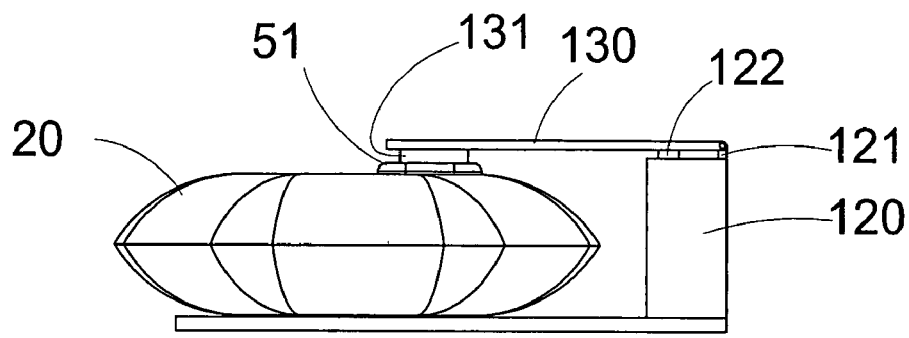
FIG. 26 is a schematic view of a second alternative mode of a protection device with a rechargeable warmer bag therein according to the above preferred embodiment of the present invention.
Figure 27:
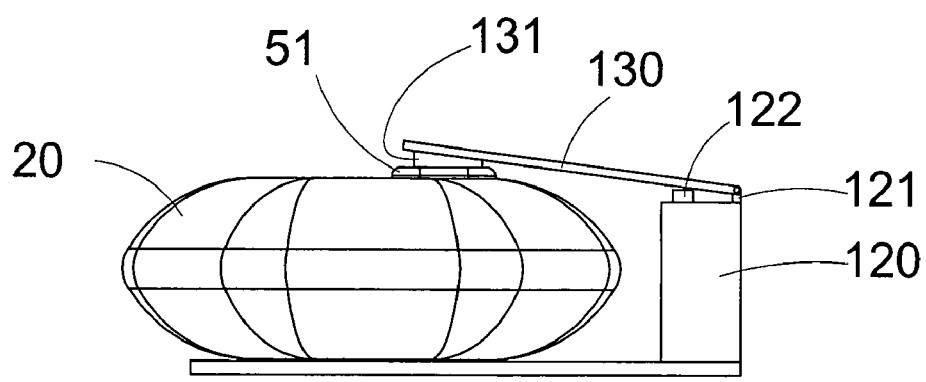
FIG. 27 is a schematic view of a second alternative mode of a protection device with an expanded rechargeable warmer bag therein according to the above preferred embodiment of the present invention.

As shown in FIG. 25 to FIG. 27, another alternative mode of the present invention is illustrated.

The protection device 100 comprises a bottom board 110, a column 120 mounted on the bottom board 110, and a connecting pole 130 connecting to the power. The column 120 comprises a connecting element 121 and an actuator switch 122 mounted on the upper side of the column 120.

The connecting pole 130 is pivotally connected on top of the column and one end of the connecting pole 130 is connected with the connecting element 121 of the column 120. When the rechargeable warmer bag 20 is being charged, the rechargeable warmer bag is positioned in the protection device 10. The other end of the connecting pole 130 is connected with the charging connector 51. The connecting pole 130 further comprises a power plug 131.

When the rechargeable warmer bag 20 is being charged, the rechargeable warmer bag 20 is disposed in the cavity 11 of the protection device 10. The power plug 131 connects to the charging connector 51 of the rechargeable warmer bag 20. At the same time, the connecting pole 130 is pushed down to turn on the actuator switch 122, and then the rechargeable warmer bag is being charged. When the rechargeable warmer bag 20 is over charged to be over-expanded, the rechargeable warmer bag 20 raises it top surface due to the expansion and presses the connecting pole 130 to move upwardly. Then, the connecting pole 130 does not press the actuator switch 122 but releasing the actuator switch 122 to cut off the power supply of the rechargeable warmer bag 20 to protect the rechargeable warmer bag from expansion.

The operating method of the warmer device of the present invention comprises the following steps.

First, open the protection device 10 having the interior protection cavity 11 isolated from outside environment.

Figure 9:
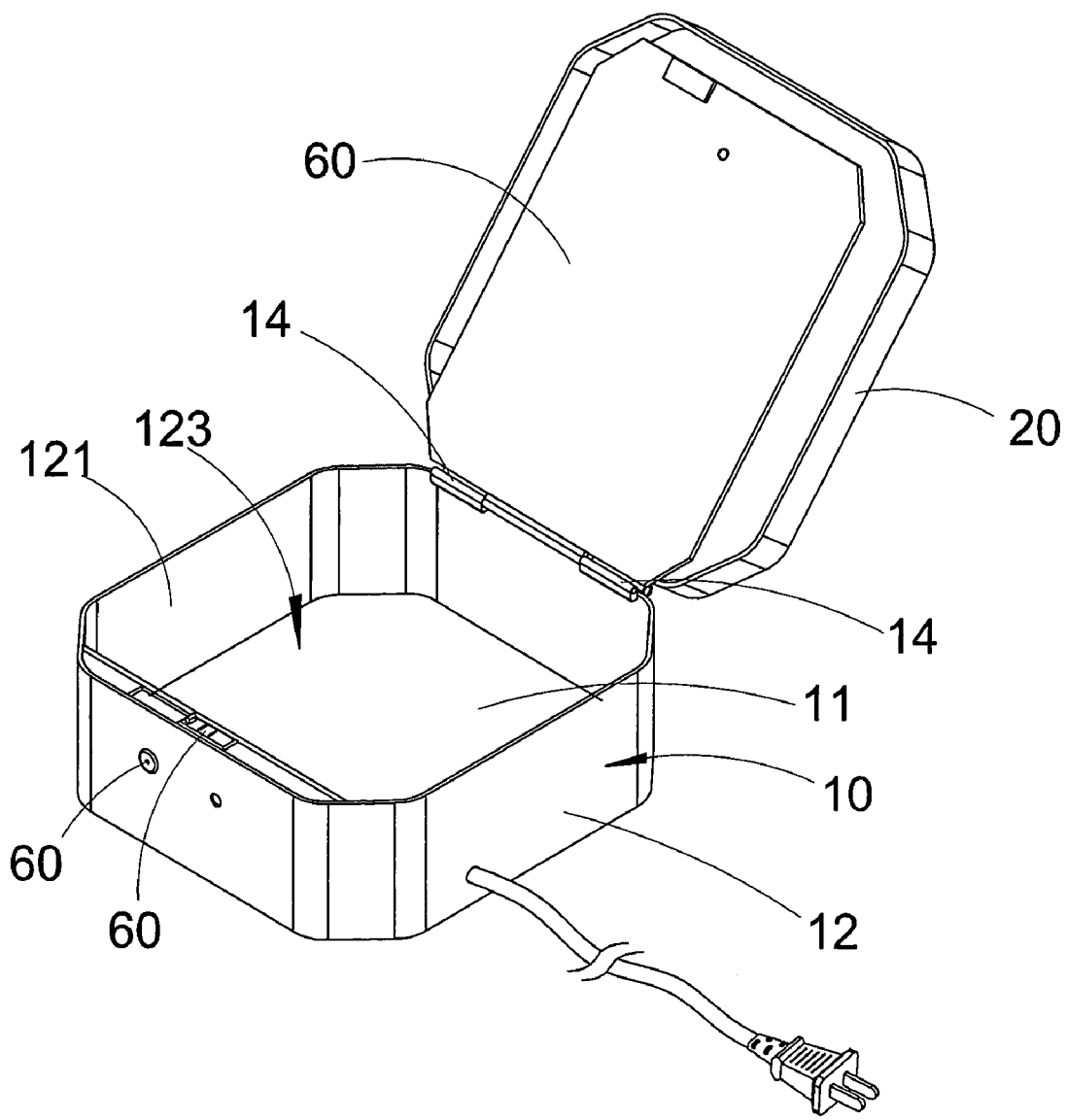
FIG. 9 is a perspective view of a protection device according to the above preferred embodiment of the present invention.
Figure 10:
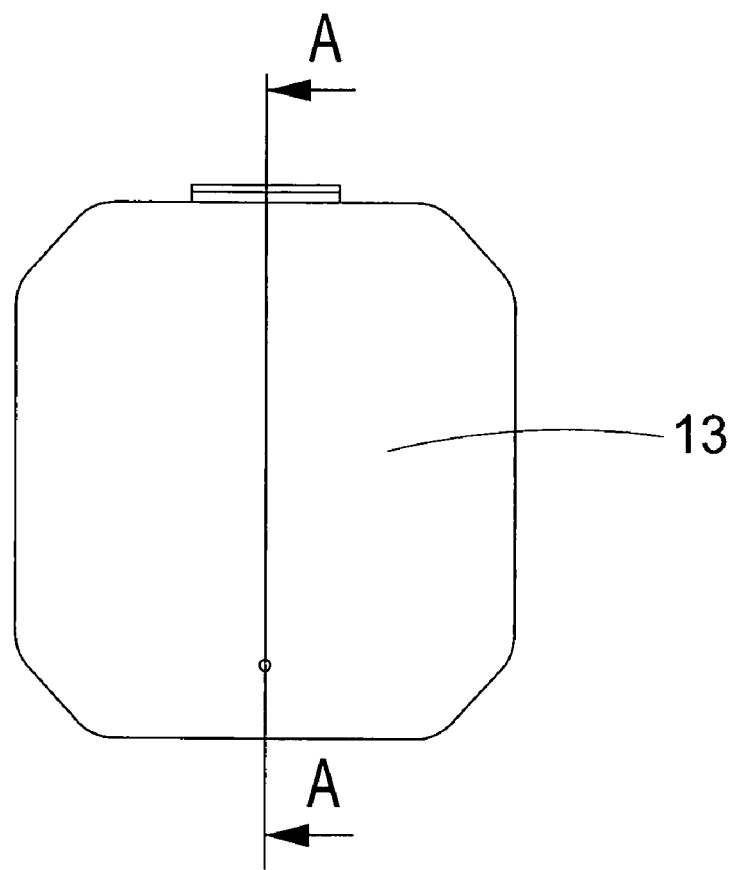
FIG. 10 is a top exterior view of the protection device according to the above preferred embodiment of the present invention.
Figure 11:
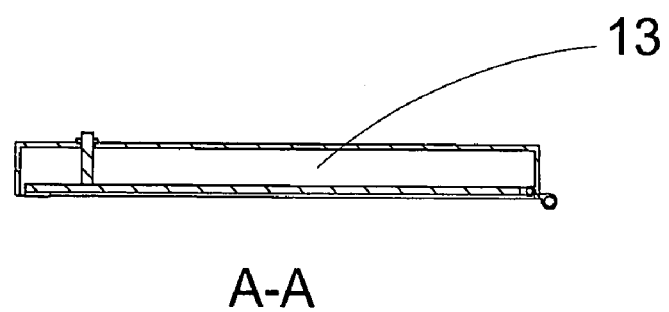
FIG. 11 is an A-A sectional view of a cover of the protection device according to the above preferred embodiment of the present invention.
Figure 12:
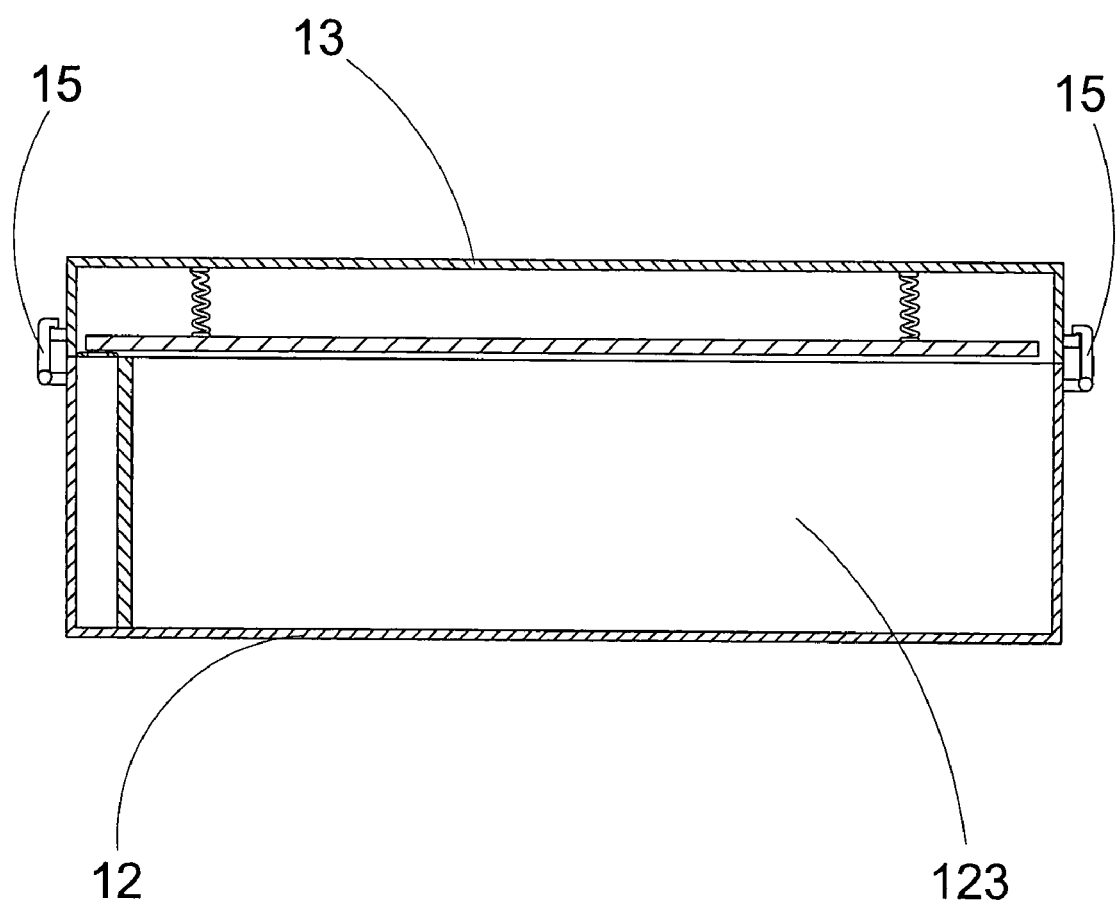
FIG. 12 is a sectional view of the protection device according to the above preferred embodiment of the present invention.

In which, as shown in FIG. 9, the protection device 10 comprises the box 12 and the box cover 13 covering the box 12, wherein the box 12 has the outer surface 122 and the inner surface 121 defining a cavity 123 separated from the outer space by the box cover 13.

Furthermore, as shown in FIG. 22, the protection device 10' further comprises the container 12' and the moving unit 13', wherein the moving unit 13' is flexibly mounted in the container 12', and can move relative to the container 12'. When the rechargeable warmer bag 20' is being charged, it is positioned in the cavity 11' of the protection device 10' and in the moving unit 13'. When the rechargeable warmer bag 20' is fully charged, the moving unit 13' moves with respect to the container 12', so that the rechargeable warmer bag 20' can be taken out of the protection device 10'.

As mentioned above, the container 12' comprises the plurality of slides 121', and the moving unit 13' comprises the plurality of slide rails 131' sliding to-and-fro on to the slides 121' of the container 12'.

Second, put the rechargeable warmer bag 20 into the protection device 10 so as to charge the rechargeable warmer bag 20.

In which, as shown in FIG. 5 to FIG. 8, the rechargeable warmer bag 20 further comprises:

the bag 30, having the outer surface 31 and the inner surface 32 defining the sealed cavity 33 receiving the predetermined amount of liquid 34 therein;

the heating unit 40 which is disposed in the liquid 34 in the sealed cavity 33 of the bag 30 comprising the plurality of heaters 41; and the charging unit 50, which is connected with the heating unit 40 and placed between the bag 30 and the heating unit 40, comprising the charging connector 51 and the connecting wire.

Furthermore, the heating unit 40 positioned in the bag 30 further comprises the connecting tube 42 and the temperature control device 43.

The temperature control device 43, which is connected between the heaters of the heating unit 40, comprises the plurality of temperature controllers 44 with different rated temperature for cutting off the power supply. When the rechargeable warmer bag 20 is being charged, the temperature control device 43 can monitor the temperature of the liquid 34 in the bag 30 in real-time. When the temperature is up to the rated temperature of any temperature controller 44, the temperature control device will cut off the power supply of the charging unit 50.

Furthermore, the connecting tube 42 is fixedly connected between the heaters 41 and the charging connector 51 of the charging unit 50 and supports the plurality of heaters 41 so as to position the heaters 41 within the sealed cavity 33 of the bag 30. When the rechargeable warmer bag 20 is being charged, the connecting tube 42 supports the heaters to ensure the heaters being disposed the sealed cavity 33 of the bag 30 and surrounded by the liquid 34 in the cavity 33.

As the heater 41 of the heating unit 40 converts the electricity to the heat, and conducts the heat to the liquid 34 in the bag 30, the temperature of the liquid 34 is raised and the volume of the liquid 34 is expanded. At this moment, the gas in the bag 30 is expanded too. According to the proportional relation of the gas expansion and liquid expansion when heated, the gas expansion velocity is faster than liquid expansion velocity, so the gas in the cavity squeezes liquid 34 in the cavity. Gradually, the heater 41 of the heating unit 40 separates from the liquid 34, as the liquid level falls due to the rising of the liquid temperature, and then the charge warmer device 20 is cut off from the power supply.

Third, put the rechargeable warmer bag 20 into the protection device 10, so as to charge the rechargeable warmer bag 20. Meanwhile, the rechargeable warmer bag 20 is monitored by a monitoring device 60. When the rechargeable warmer bag 20 is heated to overly expand, the monitoring device 60 cuts the power supply off from the charging unit 50 of the rechargeable warmer bag 20.

In which, as shown in FIG. 14 to FIG. 21, the monitoring device 60 comprises the actuator 70, the altering device 80, and the external circuit 90.

The actuator 70 is connected to the external circuit 90 and is placed in the cavity 11. When the rechargeable warmer bag 20 is being charged in the cavity 11 of the protection device 10, the rechargeable warmer bag 20 is monitored by the monitoring device 60. If rechargeable warmer bag 20 is heated to be over expanded to touch the actuator 70, the actuator 70 cuts off the power supply from the external circuit 90 so as to protect the rechargeable warmer bag 20 from being broken and explosion.

The actuator 70 comprises the actuator board 71, the actuator switch 72, and the connecting element 73, wherein the actuator board 71 is disposed in the cavity 11 of the protection device 10 and positioned above the rechargeable warmer bag 20 when being charged in the cavity 11 of the protection device.

Furthermore, the actuator board 71 is placed in the box cover 13 of the protection device 10.

One end of the actuator board 71 is pivotally connected to the top of the protection device 10.

And the actuator switch 72 and the connecting element 73 are provided on the other end of the actuator board 71, and the actuator switch 72 is connected to the external circuit 90.

The connecting element 73 can be embodied as an elastic element, such as the spring, which is connected to the box cover 13 of the protection device 10. When the rechargeable warmer bag 20 is over expanded for being charged in the protection device 10, the bag 30 is expanded upward to touch the actuator board 71 and the connecting element 73 on the other end of the actuator board 71 is compressed. And then the actuator switch 72 disconnects the external circuit 90 so as to stop charging the rechargeable warmer bag 20 to avoid the over expansion of the bag 30.

Alternatively, the connecting element 73 can be embodied a hard connecting pole, comprising the fixed pole 731 and the retaining sheet 732. The box cover 13 of the protection device 10 has the through hole 131 therein for receiving the fixed pole 731. The retaining sheet 732 is positioned on top of the fixed pole 731, bigger than the through hole 131 in size.

As mentioned above, the connecting element 73 comprises the plurality of elastic elements. One end of them connects to the top of the protection device 10, and the other end of them connects to the actuator board 71. When the rechargeable warmer bag 20 is being charged in the cavity 11 of the protection device 10, the actuator board 71 is positioned on the upper side of the protection device 10 in relative to the rechargeable warmer bag 20.

The actuator switch 72 is positioned on the actuator board 71 and connects to the external circuit 90.

Furthermore, the elastic element is embodied as the spring.

The actuator 70 comprises the actuator board 71, the actuator switch 72, and the connecting element 73, wherein the actuator board 71 is placed in the cavity 11 of the protection device 10. When the rechargeable warmer bag 20 is being charged in the cavity 11 of the protection device 10, the actuator 71 is positioned surrounding the rechargeable warmer bag 20 and the actuator switch 72 is positioned between the actuator board 71 and the external circuit 90.

The connecting element 73 is connected with the side wall of the protection device. If rechargeable warmer bag 20 is heated to be over expanded as charged in the protection device 10, the bag 30 expands to touch the actuator board 71 and compress the connecting element 73, and then the actuator switch 72 disconnects the external circuit 90 to avoid the bag 30 to be over expanded.

As mentioned above, the actuator 70 can be embodied as the temperature measuring meter. When the rechargeable warmer bag 20 is being charged in the cavity 11 of the protection device, the rechargeable warmer bag 20 is monitored by the monitoring device 60. The actuator 70 has the plurality of preset value for cutting off the power. When the rechargeable warmer bag 20 is heated to be over expanded, and the temperature of the rechargeable warmer bag 20 is up to the preset value, the actuator 70 disconnects the external circuit 90 to protect the rechargeable warmer bag 20 for being broken and explosion.

Furthermore, as shown in FIG. 22 to FIG. 24, the monitoring device 60', which is disposed in the cavity 11' of the protection device 10' and positioned between the container 12' and the moving unit 13', comprises the actuator 70', the alerting device 80', and the external circuit 90'.

The actuator 70' is connected with the external circuit 90' and positioned between container 12' and the moving unit 13'.

When the rechargeable warmer bag 20' is being charged in the cavity 11 of the protection device 10, the rechargeable warmer bag 20 is monitored by the monitoring device 60. When the rechargeable warmer bag 20' is charged to be heated, the heating bag 20' expands to compress the container to move the moving unit 12' with respect to the container 12', and then the actuator 70' between the container 12' and the moving unit 13' switches off the external circuit 90' to cut off the power supply to protect the rechargeable warmer bag 20' from being broken and explosion.

Further more the actuator 70' comprises the first contact unit 71' positioned in the container 12' and the second contact unit 72' positioned on the moving unit 13'.

The altering device 80', which is connected with the actuator 70' and the external circuit 90', comprises the visional altering device 81' and the audio alerting device 82'. When the rechargeable warmer bag 20' is being charged in the cavity 11' of the protection device, the rechargeable warmer bag 20' is monitored by the monitoring device 60'. When the rechargeable warmer bag 20' is heated to be over expanded, the actuator 70' disconnects the external circuit 90'. At the same time, the actuator 70' conducts the visional alerting device 81' and the audio alerting device 82' with the external circuit 90', so the visional alerting device 81' is illuminating and the audio alerting device 82' produces sound to alert the user.

Fourth, when the rechargeable warmer bag 20 is fully charged in the protection device 10, take the rechargeable warmer bag 20 out of the protection device, so as to detach the rechargeable warmer bag from the protection device 10.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A warmer device, comprising:

a protection device having a protection cavity therein; and
a rechargeable warmer bag which is arranged to be charged in said protection device, wherein said rechargeable warmer is disposed in said cavity of said protection device during charging and removed out of said protection device during operation, wherein said rechargeable warmer bag comprises:

a bag defining a sealed cavity therein and receiving a predetermined amount of liquid in said sealed cavity;

a heating unit which is disposed in said liquid in said sealed cavity of said bag comprising at least a heater;

a charging unit, which is connected with said heating unit and positioned between said bag and said heating unit, comprising a charging connector; and a monitoring device arranged in said protection device with respect to said rechargeable warmer bag so as to monitor said rechargeable warmer bag and cut off power supply to said charging unit of said rechargeable warmer bag when said rechargeable warmer bag is over-expanded, and that when said rechargeable warmer is in use, said rechargeable warmer bag and said monitoring device are separated;

wherein said protection device comprises a bottom board, a column mounted on said bottom board and a connecting pole connecting to the power, wherein said column comprises a connecting element and an actuator switch mounted on an upper side of said column, said connecting pole being pivotally connected on a top of said column, one end of said connecting pole being connected with said connecting element of said column, wherein when said rechargeable warmer bag is being charged, said rechargeable warmer bag is positioned in said protection device, and said other end of said connecting pole is connected with said charging connector, wherein said connecting pole further comprises a power plug, wherein when said rechargeable warmer bag is being charged, said rechargeable warmer bag is disposed in said cavity of said protection device and said power plug connects to said charging connector of said rechargeable warmer bag, and that, at the same time, said connecting pole is pushed down to turn on said actuator switch, and then said rechargeable warmer bag is being charged, wherein when said rechargeable warmer bag is over charged to over expand, said rechargeable warmer bag raises a top surface thereof due to the expansion to press said connecting pole to move upwardly, and then said connecting pole does not press said actuator switch but releasing said actuator switch to cut off the power supply of said rechargeable warmer bag.

* * * * *